United States Patent
Horiuchi et al.

(10) Patent No.: US 12,376,808 B2
(45) Date of Patent: Aug. 5, 2025

(54) RADIOGRAPHY SYSTEM AND CONTROL METHOD OF THE SAME

(71) Applicant: FUJIFILM CORPORATION, Tokyo (JP)

(72) Inventors: Hisatsugu Horiuchi, Kanagawa (JP); Koji Taninai, Kanagawa (JP); Masataka Sugahara, Kanagawa (JP); Takeyasu Kobayashi, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 606 days.

(21) Appl. No.: 17/816,994

(22) Filed: Aug. 2, 2022

(65) Prior Publication Data
US 2023/0051642 A1 Feb. 16, 2023

(30) Foreign Application Priority Data
Aug. 11, 2021 (JP) .................... 2021-131463

(51) Int. Cl.
*A61B 6/10* (2006.01)
*A61B 6/00* (2006.01)
(Continued)

(52) U.S. Cl.
CPC .......... *A61B 6/4405* (2013.01); *A61B 6/4007* (2013.01); *A61B 6/587* (2013.01); *G01T 1/17* (2013.01)

(58) Field of Classification Search
CPC ... A61B 1/00; A61B 1/00147; A61B 1/00163; A61B 6/4405; A61B 6/4435;
(Continued)

(56) References Cited

U.S. PATENT DOCUMENTS

2009/0041190 A1 2/2009 Laupper
2021/0219927 A1* 7/2021 Dencovski ............. A61B 90/35

FOREIGN PATENT DOCUMENTS

JP H11-285492 A 10/1999
JP 2005-031323 A 2/2005
(Continued)

OTHER PUBLICATIONS

English language translation of the following: Office action dated Dec. 17, 2024 from the JPO in a Japanese patent application No. 2021-131463 corresponding to the instant patent application. This office action translation is submitted now in order to supplement the understanding of the cited references which are being disclosed in the instant Information Disclosure Statement.

*Primary Examiner* — Don K Wong
(74) *Attorney, Agent, or Firm* — SOLARIS Intellectual Property Group, PLLC

(57) ABSTRACT

A radiography system includes: a radiation source that emits radiation; an imaging stand having a detection panel that generates a radiation image by detecting the radiation; a lifting device on which a subject to be examined is placed; a misalignment amount detection device that detects a relative misalignment amount between the imaging stand and the subject to be examined; and a lifting control device that lifts and lowers the lifting device on the basis of the misalignment amount detected by the misalignment amount detection device.

13 Claims, 10 Drawing Sheets

(51) Int. Cl.
*A61B 6/40* (2024.01)
*A61B 6/58* (2024.01)
*G01T 1/17* (2006.01)

(58) Field of Classification Search
CPC .... A61B 5/1113; A61B 5/1114; A61B 5/1115; A61B 5/1116; A61B 6/4452; A61B 6/4429
See application file for complete search history.

(56) References Cited

FOREIGN PATENT DOCUMENTS

| | | |
|---|---|---|
| JP | 2005-177211 A | 7/2005 |
| JP | 2006-43193 A | 2/2006 |
| JP | 2008-161234 A | 7/2008 |
| JP | 2009-517098 A | 4/2009 |
| JP | 2011-67509 A | 4/2011 |
| JP | 2011-125544 A | 6/2011 |
| KR | 10-2018-0124652 A | 11/2018 |

* cited by examiner

LIFTING CONTROL

LIFTING CONTROL

FIG. 14

| IMAGING MENU | FEATURE SITE | TARGET REGION 70 | |
|---|---|---|---|
| | | WIDTH | CENTER COORDINATES |
| CHEST | VERTEBRA PROMINENS | 40 mm | UPPER SIDE OF IMAGE |
| WAIST | COCCYX | 60 mm | LOWER SIDE OF IMAGE |
| HEAD | CENTER OF GRAVITY OF OUTLINE OF HEAD | 30 mm | CENTER OF IMAGE |

RADIOGRAPHY SYSTEM AND CONTROL METHOD OF THE SAME

CROSS-REFERENCE TO RELATED APPLICATIONS

The present application claims priority under 35 U.S.C. § 119 to Japanese Patent Application No. 2021-131463 filed on Aug. 11, 2021. The above application is hereby expressly incorporated by reference, in its entirety, into the present application.

BACKGROUND

1. Technical Field

A technique of the present disclosure relates to a radiography system and a control method of the same.

2. Description of the Related Art

Due to the recent epidemic of the new coronavirus, infection outbreaks called clusters are occurring in medical institutions as well. For this reason, it is preferable to appropriately align a subject to be examined, such as a patient, with respect to an imaging stand while reducing the chance of contact between the subject to be examined and a technician from the viewpoint of preventing infectious diseases, in a case where radiographing the subject to be examined at a medical institution. However, in the present circumstances, since the technician enters a radiation room and directly aligns the subject to be examined, there are many chances of contact between the subject to be examined and the technician.

There is known a radiography system comprising a lifting device that lifts and lowers a lifting table on which a subject to be examined is placed with respect to an imaging stand, as a technique that enables a technician to align the subject to be examined without coming into contact with the subject to be examined (see, for example, JP2005-177211A and JP2005-031323A).

SUMMARY

In the radiography systems disclosed in JP2005-177211A and JP2005-031323A, there is a problem in the safety of the subject to be examined in a case where the technician is low-skilled because the technician aligns the subject to be examined by manually operating the lifting device while confirming the lifting device. Alternatively, there arises a problem regarding the safety of the subject to be examined, such as unintended inching, in a case where the lifting device is automatically controlled and is lifted and lowered without confirmation of the technician.

An object of the technique of the present disclosure is to provide a radiography system and a control method of the same capable of reducing the chance of contact between a subject to be examined and a technician and safely aligning the subject to be examined.

There is provided a radiography system of the present disclosure comprising: a radiation source that emits radiation; an imaging stand having a detection panel that generates a radiation image by detecting the radiation; a lifting device on which a subject to be examined is placed; a misalignment amount detection device that detects a relative misalignment amount between the imaging stand and the subject to be examined; and a lifting control device that lifts and lowers the lifting device on the basis of the misalignment amount detected by the misalignment amount detection device.

It is preferable that the lifting control device controls the lifting device in a direction of lowering the lifting device from an initial position and in a direction of reducing the misalignment amount.

It is preferable that the lifting control device controls a lifting speed of the lifting device according to the misalignment amount.

It is preferable that the lifting control device makes the lifting speed high in a case where the misalignment amount is large, and makes the lifting speed low in a case where the misalignment amount is small.

It is preferable that the lifting control device detects a body motion of the subject to be examined on the basis of the lifting speed and a change in the misalignment amount.

It is preferable that the lifting control device detects a difference between the lifting speed and the change in the misalignment amount, as a body motion speed of the subject to be examined, and makes the lifting speed a certain value or less in a case where the detected body motion speed is a certain speed or higher.

It is preferable that the misalignment amount detection device includes a camera provided on the radiation source and imaging the subject to be examined, and an image analysis device that detects the misalignment amount by analyzing an image acquired by the camera.

It is preferable that the image analysis device detects a feature site of the subject to be examined from the image, and detects the misalignment amount on the basis of a difference between a position of the detected feature site and a target region on the imaging stand.

It is preferable that the feature site is an anatomical feature of the subject to be examined or a marker provided on an examination gown.

It is preferable that the feature site and the target region are set in advance for each imaging menu, and the image analysis device selects the feature site and the target region for detecting the misalignment amount, according to the imaging menu.

It is preferable that the lifting control device stops lifting and lowering the lifting device in a case where the subject to be examined is predicted to collide with an object on the basis of the image.

It is preferable that the lifting control device gives a warning in a case where the subject to be examined is predicted to collide with an object on the basis of the image.

There is provided a control method of a radiography system of the present disclosure including a radiation source that emits radiation, an imaging stand having a detection panel that generates a radiation image by detecting the radiation, a lifting device on which a subject to be examined is placed, and a misalignment amount detection device that detects a relative misalignment amount between the imaging stand and the subject to be examined, the control method comprising: lifting and lowering the lifting device on the basis of the misalignment amount detected by the misalignment amount detection device.

According to the technique of the present disclosure, it is possible to provide a radiography system and a control method of the same capable of reducing the chance of contact between a subject to be examined and a technician and safely aligning the subject to be examined.

BRIEF DESCRIPTION OF THE DRAWINGS

Exemplary embodiments according to the technique of the present disclosure will be described in detail based on the following figures, wherein:

FIG. 14 is a diagram showing an example of a setting table in which the feature site and the target region are set for each imaging menu.

DETAILED DESCRIPTION

Figure 1:
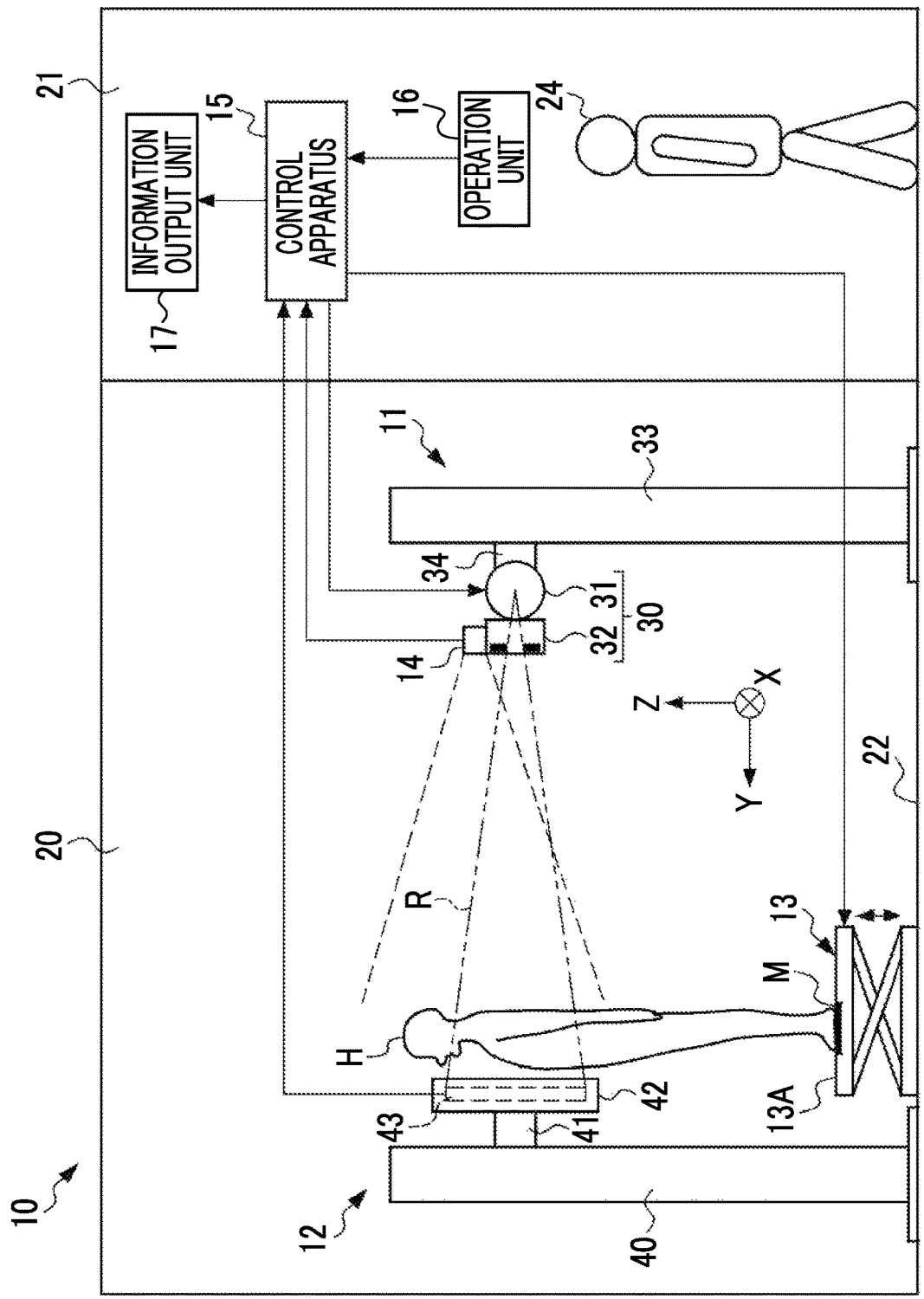
FIG. 1 is a schematic diagram showing an example of a configuration of a radiography system.

As shown in FIG. 1 as an example, a radiography system 10 comprises a radiation generation device 11, an imaging stand 12, a lifting device 13, a camera 14, a control apparatus 15, an operation unit 16, and an information output unit 17. The radiation generation device 11, the imaging stand 12, the lifting device 13, and the camera 14 are provided in a radiation room 20 in which radiography with respect to a subject to be examined H is performed. The control apparatus 15, the operation unit 16, and the information output unit 17 are provided in an operation room 21 adjacent to the radiation room 20. The control apparatus 15 may be provided in the radiation room 20.

A window (not shown) is provided between the radiation room 20 and the operation room 21. A technician 24 gives an instruction to start aligning the subject to be examined H with respect to the imaging stand 12 and an instruction to start radiographing the subject to be examined H by operating the operation unit 16 while confirming the inside of the radiation room 20 through the window, in the operation room 21.

The radiation generation device 11 includes a radiation source 30. The radiation source 30 is composed of a radiation tube 31 and a collimator 32. The radiation tube 31 generates radiation R in response to the application of high voltage current. The radiation R is, for example, X-rays. In addition, the collimator 32 is attached to the emission side of the radiation tube 31. The collimator 32 is an irradiation field limiting device configured to narrow the irradiation range of the radiation R emitted from the radiation tube 31. The collimator 32 is formed by, for example, combining a plurality of flat plates made of lead or the like.

In the present embodiment, the radiation source 30 is held by a stand 33 installed on a floor surface 22 of the radiation room 20. The stand 33 is connected to the radiation source 30 through a connecting portion 34. The radiation source 30 is held by the stand 33 so as to be movable in the vertical direction (Z direction). The stand 33 is attached to a floor traveling device (not shown). That is, the radiation generation device 11 of the present embodiment is a floor traveling type.

The radiation source 30 is connected to the control apparatus 15 in a wired or wireless manner. The control apparatus 15 causes the radiation source 30 to generate the radiation R in response to the operation of the operation unit 16 performed by the technician 24.

In the present embodiment, the imaging stand 12 is an upright imaging stand that is used to image the subject to be examined H in an upright posture. The imaging stand 12 has a stand 40, a connecting portion 41, and a holder 42. The stand 40 is installed on the floor surface 22 of the radiation room 20. The stand 40 is connected to the holder 42 through the connecting portion 41. The holder 42 is held by the stand 40 so as to be movable in the vertical direction.

The holder 42 has a box shape and houses a detection panel 43 therein. The holder 42 is mostly formed of a conductive material having an electromagnetic wave shielding property, such as aluminum or stainless steel. Further, the holder 42 has a front surface facing the radiation source 30, and the front surface is mostly formed of a material transmitting the radiation R, such as carbon. The holder 42 has a size conforming to the international standard International Organization for Standardization (ISO) 4090:2001, as in, for example, a film cassette, an imaging plate (IP) cassette, and a computed radiography (CR) cassette.

The detection panel 43 is a so-called radiation flat panel detector (FPD). The detection panel 43 as an example is an indirect conversion type radiation FPD that converts radiation into visible light through a scintillator and that converts the visible light into electric charge through a photodiode. The detection panel 43 may be a direct conversion type radiation FPD that directly converts radiation into electric charge through a conversion layer, such as amorphous selenium (a-Se).

The detection panel 43 has a built-in battery and is portable. Further, the detection panel 43 comprises a dose detection sensor detecting the irradiation dose of the radiation R, and detects the start of the irradiation of the radiation R from the radiation source 30 by itself to start a radiography operation. The detection panel 43 generates a radiation image by detecting the radiation R emitted from the radiation source 30 and transmitted through the imaging site of the subject to be examined H.

The detection panel 43 is connected to the control apparatus 15 in a wired or wireless manner. The detection panel 43 transmits the generated radiation image to the control apparatus 15 after the end of the radiography.

The radiation generation device 11 and the imaging stand 12 are disposed such that the radiation source 30 and the detection panel 43 are separated from each other by a certain distance in the horizontal direction (V direction). The positions of the radiation generation device 11 and the imaging stand 12 are set such that the irradiation range of the radiation R is included in the detection surface of the detection panel 43.

The lifting device 13 is installed on the floor surface 22 of the radiation room 20. Specifically, the lifting device 13 is installed between the radiation generation device 11 and the imaging stand 12 at a position close to the imaging stand 12. The lifting device 13 is lifted and lowered in a state in which the subject to be examined H is placed so that the subject to be examined H can be aligned in the vertical direction. A marker M indicating an appropriate standing position of the subject to be examined H is formed on a top plate 13A of the lifting device 13.

The lifting device 13 is connected to the control apparatus 15 in a wired or wireless manner. The control apparatus 15 detects a relative misalignment amount between the imaging stand 12 and the subject to be examined H on the basis of the image acquired by the camera 14, and lifts and lowers the lifting device 13 on the basis of the detected misalignment amount.

The camera 14 is an imaging device that optically images the subject to be examined H placed on the lifting device 13. The camera 14 is, for example, a digital camera having a built-in complementary metal oxide semiconductor (CMOS) image sensor, and captures an image of visible light. The camera 14 is not limited to visible light, and may be an infrared camera that captures an infrared image.

The camera 14 is attached to, for example, the radiation source 30 such that the visual field range of the camera 14 includes the holder 42 holding the detection panel 43. Specifically, the camera 14 is attached to the collimator 32. The camera 14 is connected to the control apparatus 15 in a wired or wireless manner.

The control apparatus 15 is, for example, a console installed in the operation room 21. The console is a computer including a processor, such as a central processing unit (CPU), a memory, and a storage device. The storage device stores a program for operating the processor. The operation unit 16 is an input device, such as a keyboard, a mouse, and a switch. The information output unit 17 is an output device, such as a display and a speaker.

The operation unit 16 is configured to receive an input operation from the technician 24. The technician 24 operates the operation unit 16 so that the technician 24 can give an instruction to start aligning the subject to be examined H through the lifting device 13 and an instruction to emit the radiation R through the radiation source 30 (that is, an instruction to start radiography).

Figure 2:
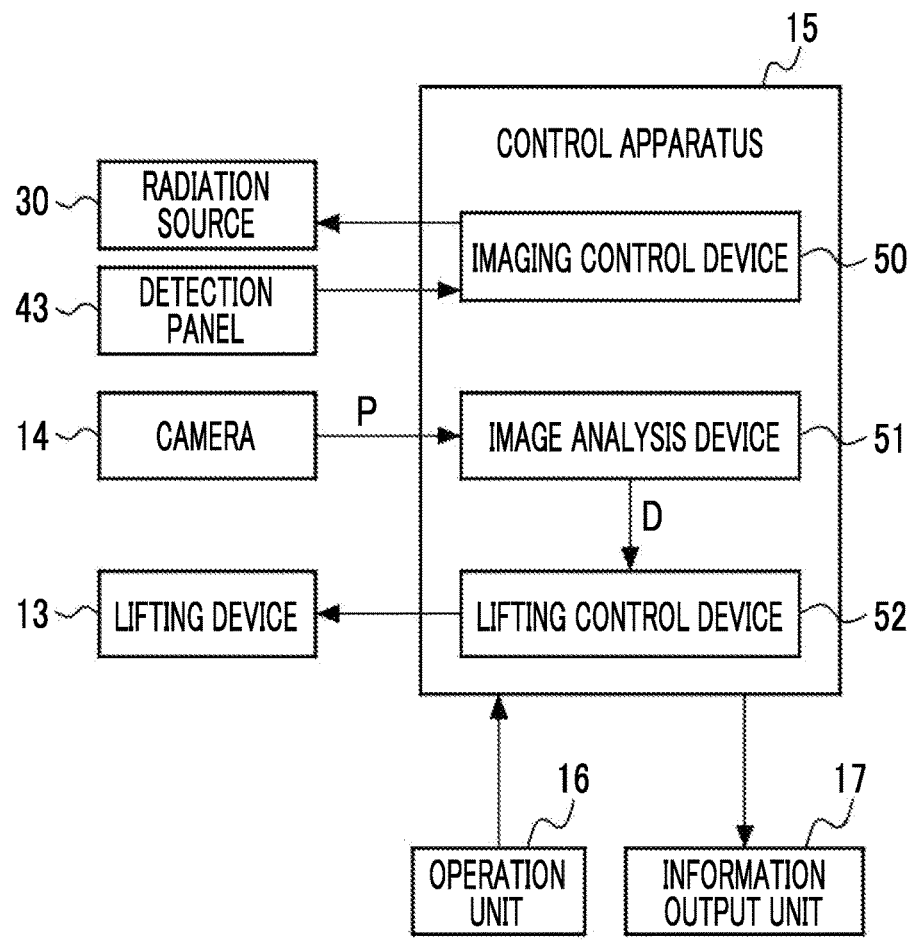
FIG. 2 is a block diagram showing an example of a configuration of a control apparatus.

As shown in FIG. 2 as an example, the control apparatus 15 is composed of an imaging control device 50, an image analysis device 51, and a lifting control device 52. The processor executes processing on the basis of the program, whereby the function of each device is realized. The imaging control device 50, the image analysis device 51, and the lifting control device 52 may be formed as separate devices. Further, in a case where the control apparatus 15 is composed of a plurality of devices, a part of the plurality of devices may be installed in the radiation room 20 and the other device may be installed in the operation room 21.

An imaging menu is input to the imaging control device 50 by the technician 24 or the like. The imaging control device 50 performs control related to radiography through the radiation source 30 and the detection panel 43, on the basis of irradiation conditions corresponding to the input imaging menu. Further, the imaging control device 50 receives the radiation image transmitted from the detection panel 43, and causes the information output unit 17 to display the received radiation image.

The imaging control device 50 is communicably connected to a radiology information system (RIS) through a network, such as a local area network (LAN). The imaging control device 50 receives an imaging order from the RIS. The imaging order includes the imaging menu and the patient information of the subject to be examined H. Further, the imaging control device 50 is communicably connected to an image database server (not shown) through the network. The image database server is, for example, a picture archiving and communication system (PACS) server, and receives the radiation image from the imaging control device 50 to accumulate and manage the received radiation image.

The image analysis device 51 analyzes an image P acquired by the camera 14 to detect the relative misalignment amount D between the imaging stand 12 and the subject to be examined H, and outputs the detected misalignment amount D to the lifting control device 52.

The lifting control device 52 controls the lifting and lowering of the lifting device 13 such that the misalignment amount D approaches zero, on the basis of the misalignment amount D input from the image analysis device 51.

Figure 3:
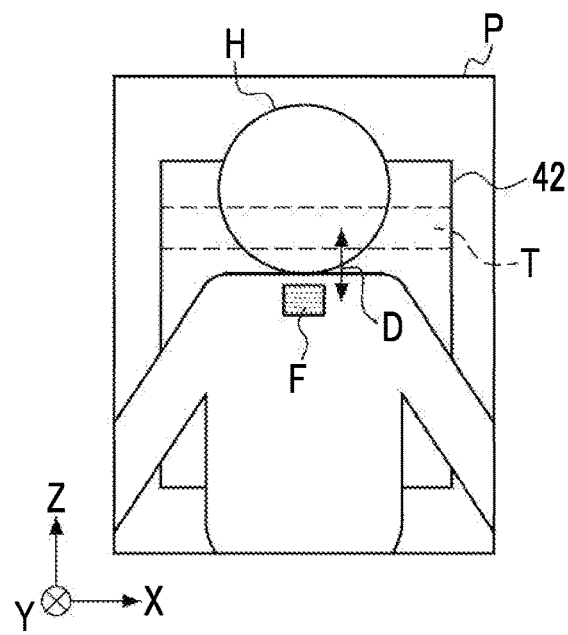
FIG. 3 is a schematic diagram showing an example of detection processing of a misalignment amount performed by an image analysis device.

FIG. 3 shows an example of the detection processing of the misalignment amount D performed by the image analysis device 51. The image analysis device 51 acquires the image P from the camera 14 and detects a feature site F representing the anatomical feature of the subject to be examined H appearing in the image P. In the present embodiment, the chest of the subject to be examined H is imaged in the upright posture in the PA direction. In the present embodiment, the feature site F is "vertebra prominens". The image analysis device 51 detects the feature site F through a method such as pattern matching or machine learning.

Further, the image analysis device 51 detects the feature site F from the image P, and then detects the misalignment amount D on the basis of the difference between the position of the feature site F and the target region T on the imaging stand 12. In the present embodiment, the target region T is set to the upper side of the image P with respect to the middle of the image P (on the +Z direction side) in a region corresponding to the detection panel 43. For example, the target region T is a rectangular region extending in an X direction. The width of the target region T in the Z direction is, for example, 40 mm.

The image analysis device 51 measures the difference between the feature site F and the target region T in the Z direction, in the image P. The difference obtained by the measurement is the misalignment amount D. As described above, the camera 14 and the image analysis device 51 constitute the "misalignment amount detection device" according to the technique of the present disclosure.

Figure 4:
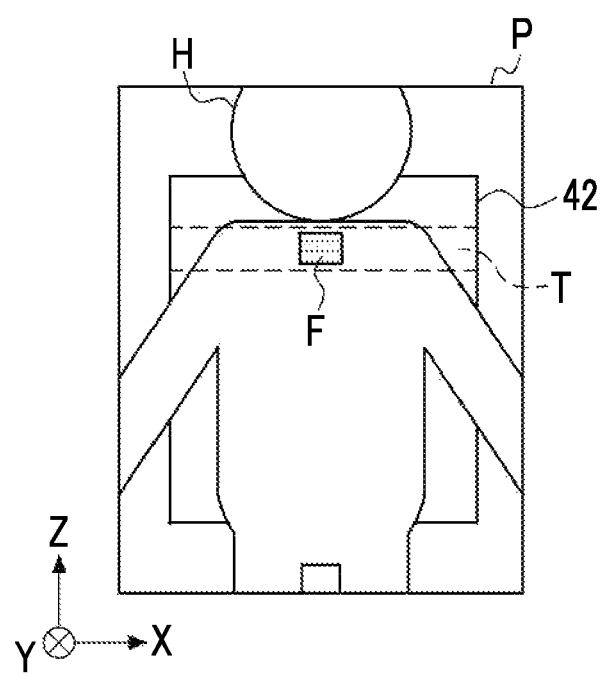
FIG. 4 is a schematic diagram showing an example of a state in which a feature site exists in a target region.

FIG. 4 shows an example of a state in which the feature site F exists in the target region T, that is, a state in which the misalignment amount D is zero. The lifting control device 52 controls the lifting and lowering of the lifting device 13 such that the misalignment amount D approaches zero and finally becomes zero. In the present embodiment, the state in which the misalignment amount D is zero is a state in which the chest of the subject to be examined H faces the detection panel 43 straight, which is suitable for chest imaging.

Figure 5:
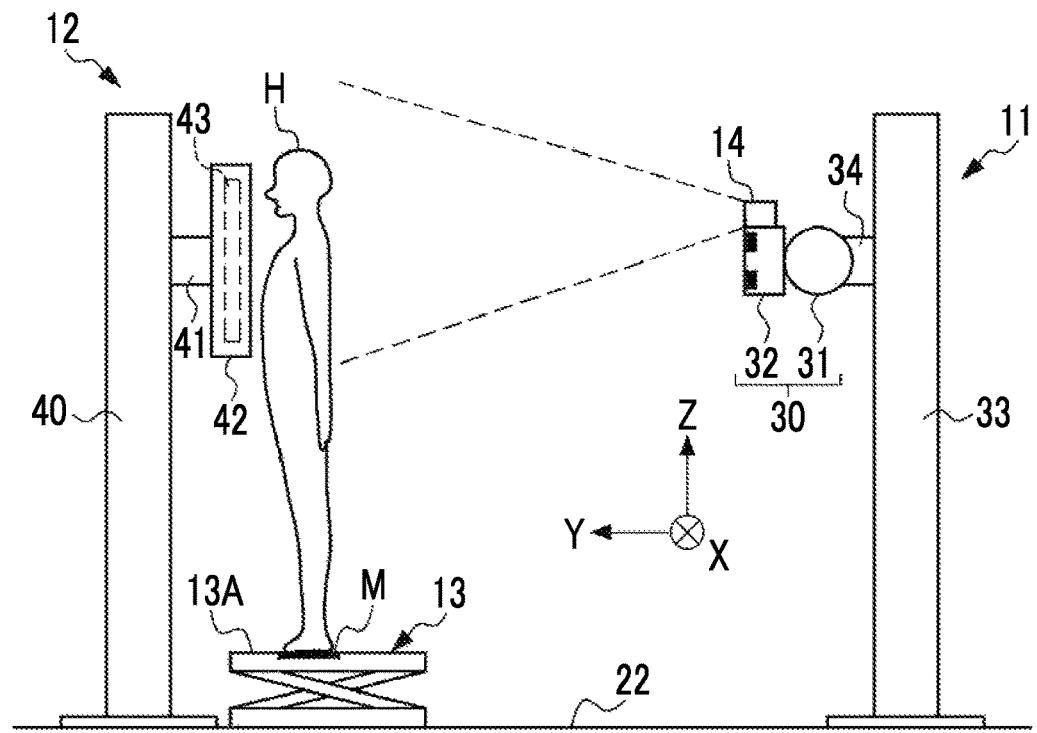
FIG. 5 is a schematic diagram showing an example of lifting control of a lifting device performed by a lifting control device.
Figure 5:
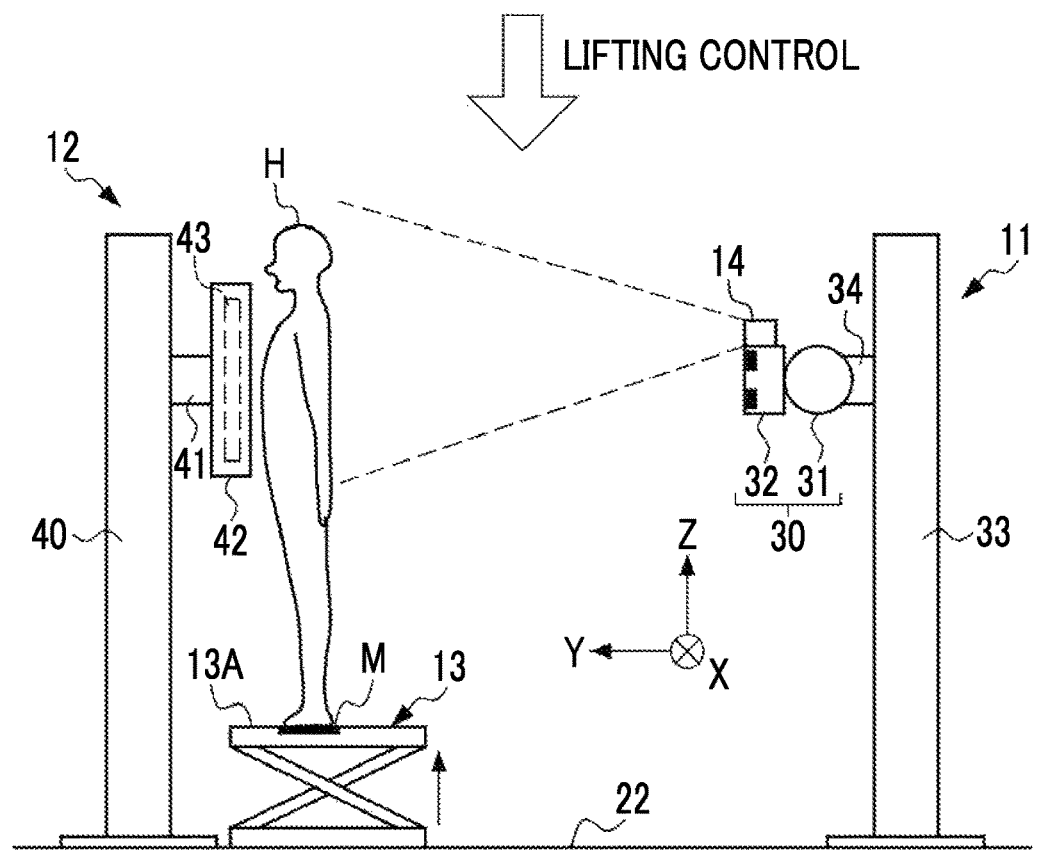

FIG. 5 shows an example of lifting control of the lifting device 13 performed by the lifting control device 52. In the present embodiment, the lifting control device 52 sets the lowest position of the top plate 13A of the lifting device 13 as the initial position so that the subject to be examined H can easily get on the top plate 13A of the lifting device 13. The lifting control device 52 controls the lifting device 13 in the direction of raising the lifting device 13 from the initial position and in the direction of reducing the misalignment amount D, after the subject to be examined H has gotten on the lifting device 13.

Figure 6:
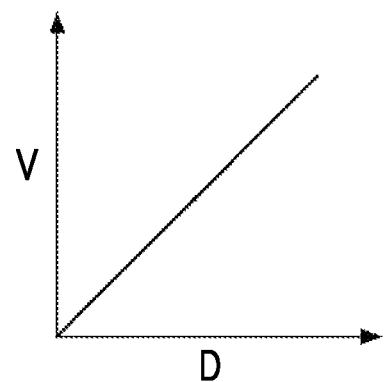
FIG. 6 is a graph showing an example of a relationship between a lifting speed and the misalignment amount in the lifting control.

FIG. 6 shows an example of the relationship between a lifting speed V and the misalignment amount D in the lifting control. The lifting control device 52 controls the lifting speed V of the lifting device 13 according to the misalignment amount D in order to prevent the lifting device 13 from suddenly stopping and enhance the safety of the subject to be examined H. Specifically, as shown in FIG. 6 as an example, the lifting control device 52 makes the lifting speed V high in a case where the misalignment amount D is large, and makes the lifting speed V low in a case where the misalignment amount D is small. In FIG. 6, the relationship between the lifting speed V and the misalignment amount D is linear, but the relationship between the lifting speed V and the misalignment amount D may be non-linear. Further, the lifting control device 52 may control the lifting and lowering of the lifting device 13 through proportional-integral-differential (PID) control.

Figure 7:
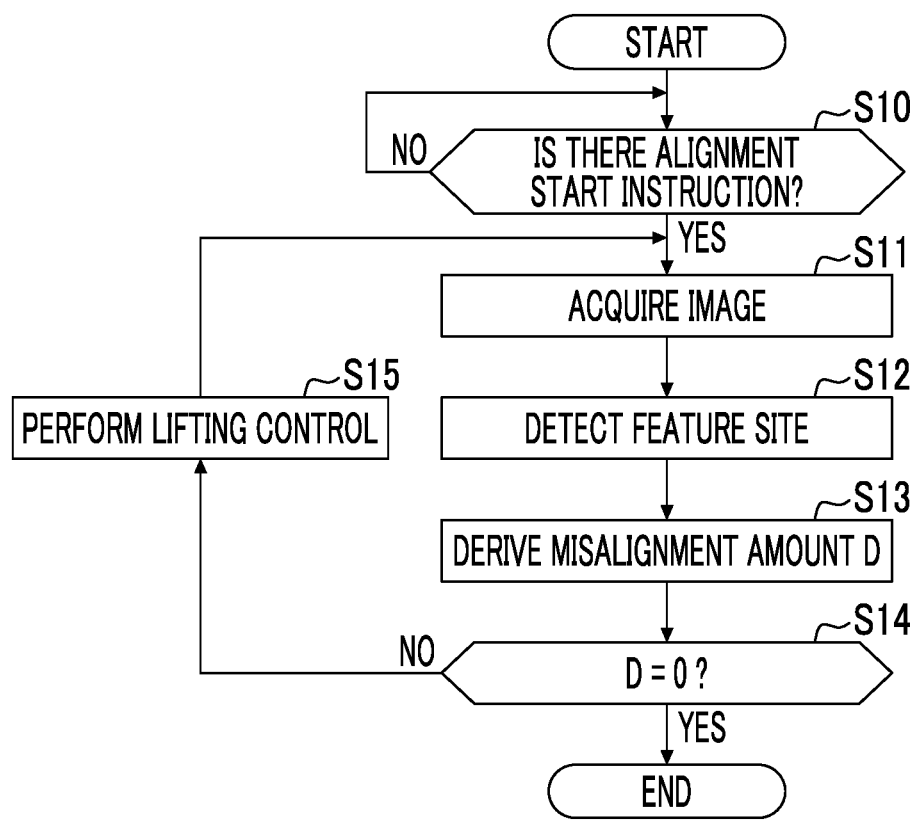
FIG. 7 is a flowchart showing an example of an operation of aligning a subject to be examined through the radiography system.

FIG. 7 is a flowchart showing an example of an operation of aligning the subject to be examined H through the radiography system 10 having the above configuration. First, the technician 24 in the operation room 21 instructs the subject to be examined H in the radiation room 20 to get on the top plate 13A of the lifting device 13. The technician 24 confirms that the subject to be examined H is standing at an appropriate position in accordance with the marker M on the top plate 13A, and then operates the operation unit 16 to start aligning the subject to be examined H with respect to the imaging stand 12.

The control apparatus 15 determines whether or not the alignment start instruction is given from the operation unit 16 (step S10). In a case where the control apparatus 15 determines that the alignment start instruction is given (step S10: YES), the image analysis device 51 acquires the image P captured by the camera 14 (step S11).

The image analysis device 51 detects the feature site F from the acquired image P (step S12). The image analysis device 51 derives the misalignment amount D on the basis of the detected position of the feature site F and the position of the target region T (step S13).

The lifting control device 52 determines whether or not the misalignment amount D derived by the image analysis device 51 is zero (step S14), and controls the lifting and lowering of the lifting device 13 (step S15) such that the misalignment amount D approaches zero in a case where the misalignment amount D is not zero (step S14: NO). After that, the process returns to step S11, and the image analysis device 51 acquires the image P captured by the camera 14.

Steps S11 to S15 are repeatedly performed until determination is made in step S14 that the misalignment amount D is zero. The alignment operation ends in a case where determination is made in step S14 that the misalignment amount D is zero (step S14: YES).

The technician 24 causes the imaging control device 50 to execute radiography by operating the operation unit 16 after the end of the alignment for the subject to be examined H.

As described above, with the radiography system 10 of the present disclosure, the technician 24 can accurately align the subject to be examined H without coming into contact with the subject to be examined H. Therefore, it is possible to reduce the chance of contact between the subject to be examined H and the technician 24 and to safely align the subject to be examined H.

A configuration may be adopted in which the technician 24 can finely adjust the height of the subject to be examined H by controlling the lifting and lowering the lifting device 13 by using the operation unit 16 after the end of the alignment for the subject to be examined H.

Hereinafter, various modification examples of the above embodiment will be described.

First Modification Example

Figure 8:
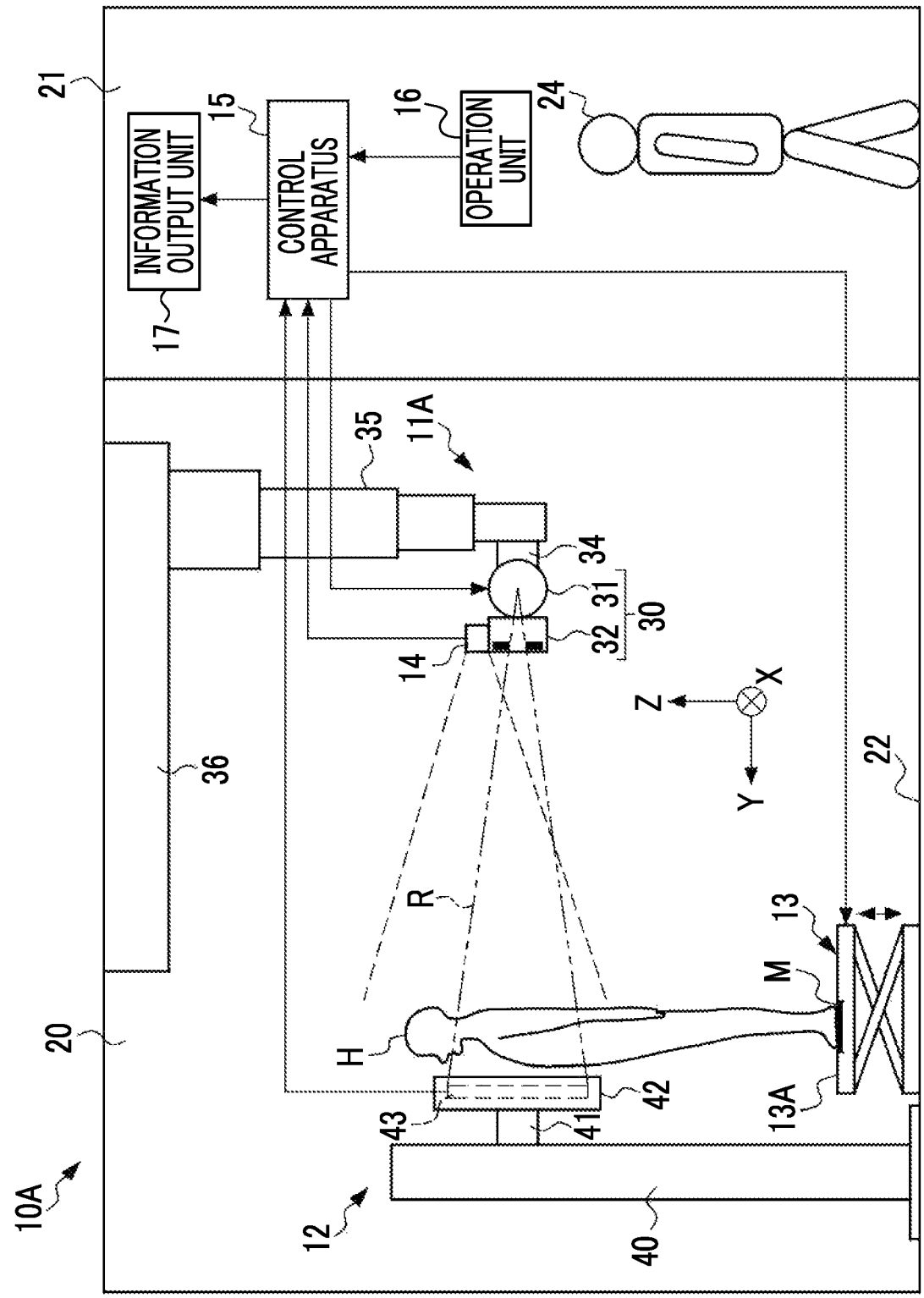
FIG. 8 is a schematic diagram showing a configuration of a radiography system according to a first modification example.

In the above embodiment, a floor traveling type is used as the radiation generation device 11, but a ceiling traveling type may be used. FIG. 8 shows the configuration of a radiography system 10A according to a first modification example. The radiography system 10A comprises a ceiling traveling type radiation generation device 11A. The radiation generation device 11A has an arm 35 that expands and contracts in the Z direction. The radiation source 30 is connected to the lower end of the arm 35 through the connecting portion 34. The upper end of the arm 35 is connected to a ceiling traveling device 36.

The radiation source 30 can move in a Y direction through the ceiling traveling device 36. The radiation generation device 11A may have an auto-tracking function for making the height of the radiation source 30 follow the height of the holder 42 of the imaging stand 12 by expanding and contracting the arm 35.

Second Modification Example

In the above embodiment, the lifting control device 52 sets the lowest position of the top plate 13A of the lifting device 13 as the initial position, but the lifting control device 52 sets the highest position of the top plate 13A of the lifting device 13 as the initial position, in a second modification example. That is, in the second modification example, the lifting control device 52 controls the lifting device 13 in the direction of lowering the lifting device 13 from the initial position and in the direction of reducing the misalignment amount D, in the alignment operation.

Figure 9:
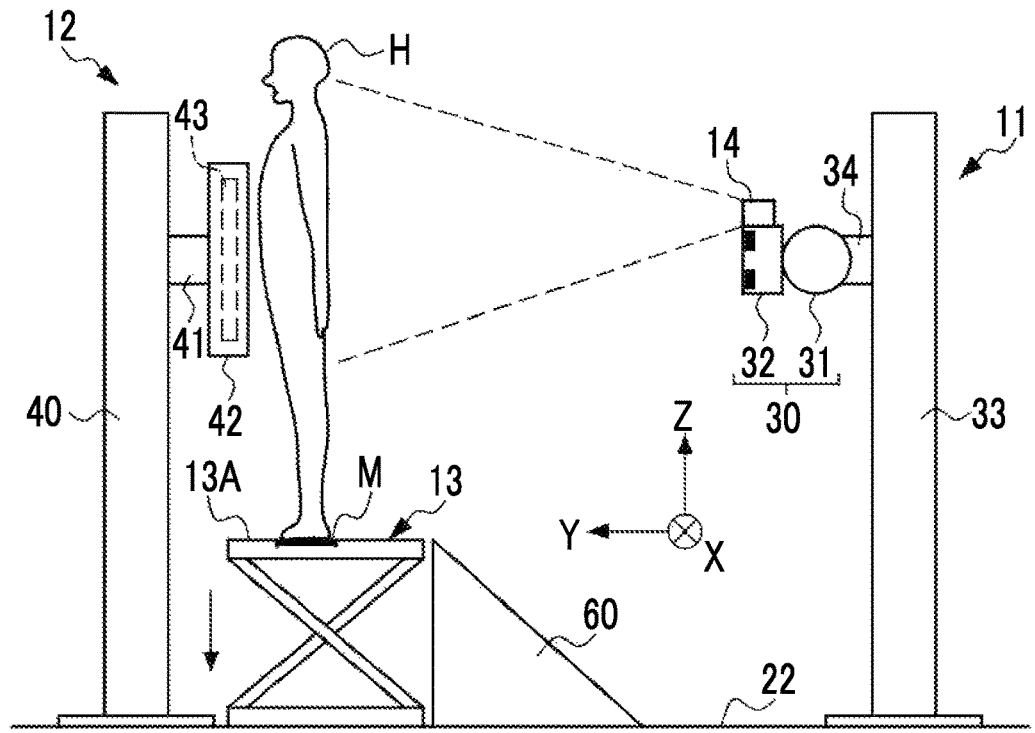
FIG. 9 is a schematic diagram showing lifting control according to a second modification example.
Figure 9:
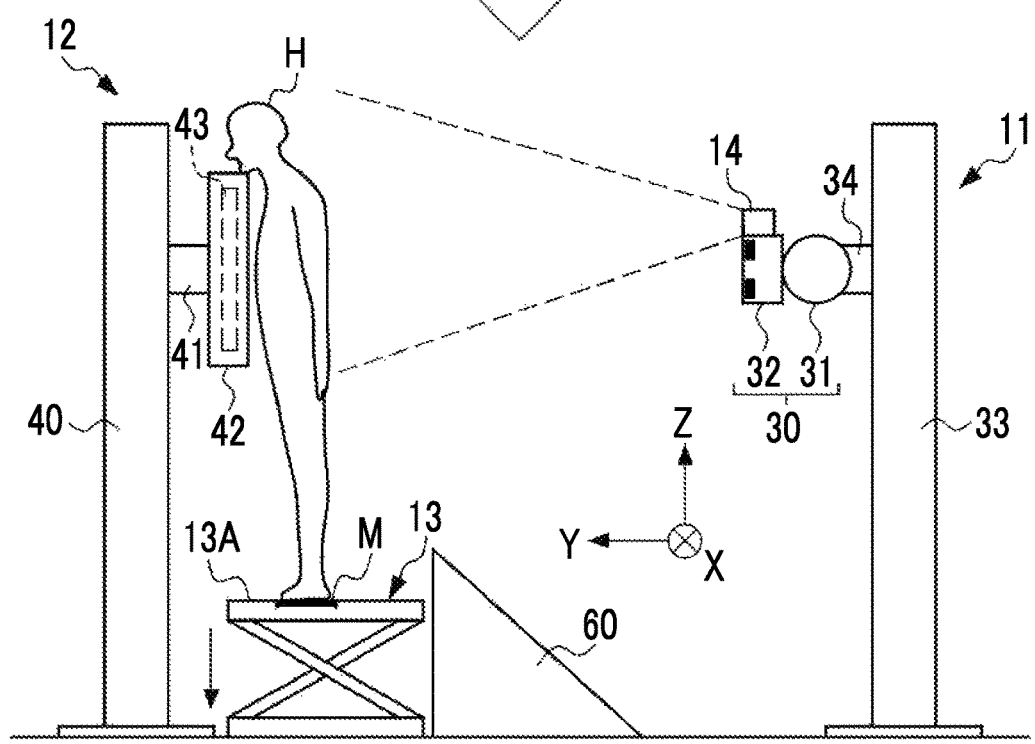

FIG. 9 shows lifting control according to the second modification example. As described above, in the second modification example, since the initial position of the lifting device 13 is the highest position of the top plate 13A, a slope 60 is disposed so as to be close to the lifting device 13 such that the subject to be examined H easily gets on the lifting device 13. The subject to be examined H can get on the lifting device 13 by using the slope 60.

In a case where the initial position is high, the feature site F is located above the target region T in a state in which the subject to be examined H is on the lifting device 13. Therefore, the lifting control device 52 controls the lifting device 13 in the direction of lowering the lifting device 13 from the initial position.

In this way, the lifting control device 52 sets the initial position high and controls the lifting device 13 in the direction of lowering the subject to be examined H to perform the alignment, whereby the positioning is performed in a state in which the chin of the subject to be examined H is in contact with the upper part (chin rest) of the holder 42. The lifting control device 52 controls the lifting device 13 in the direction of lowering the subject to be examined H from a high position, so that the chin rest facilitates positioning even without the assistance of the technician 24, and the safety is improved.

Figure 10:
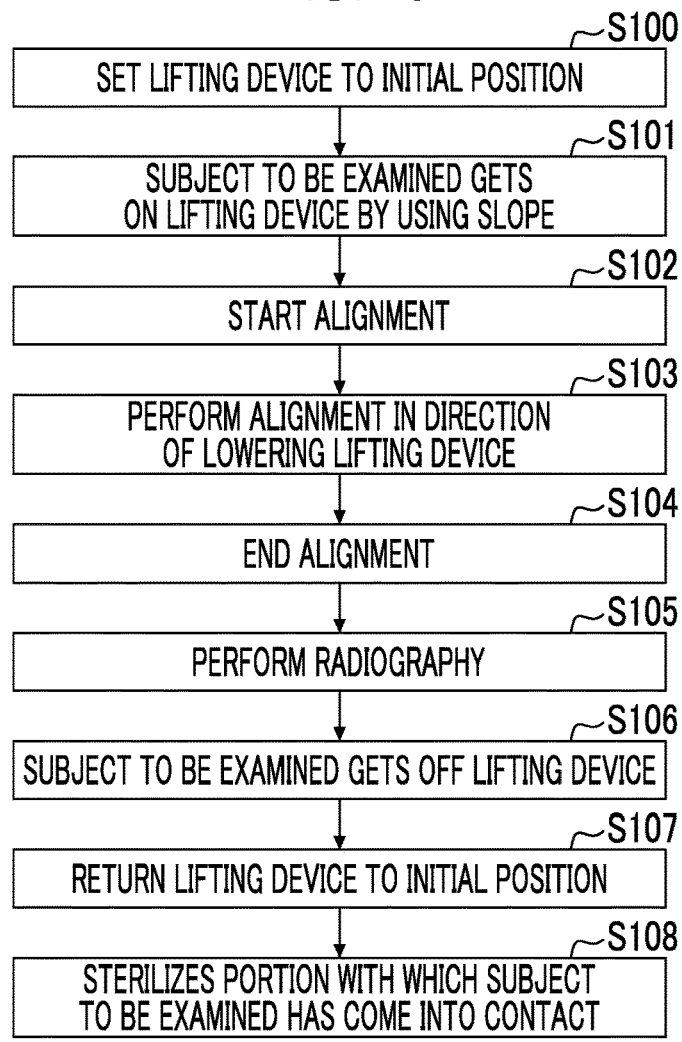
FIG. 10 is a flowchart showing a procedure of alignment and imaging in the second modification example.

FIG. 10 shows the procedure of the alignment and the imaging in the second modification example. First, the technician 24 operates the operation unit 16 to set the lifting device 13 to the initial position (step S100). The initial position is the highest position of the top plate 13A. After the lifting device 13 is set to the initial position, the subject to be examined H gets on the lifting device 13 by using the slope 60 (step S101). At this time, the subject to be examined H stands in an appropriate position in accordance with the marker M on the top plate 13A.

Next, the technician 24 operates the operation unit 16 to start aligning the subject to be examined H through the lifting device 13 (step S102). In a case where the control apparatus 15 receives alignment start instruction from the operation unit 16, the control apparatus 15 performs the alignment in the direction of lowering the lifting device 13 (step S103). The alignment control performed by the control apparatus 15 is the same as that of the above embodiment except that the directions of lifting and lowering the lifting device 13 are different from each other. The alignment ends in a state in which the chin of the subject to be examined H is in contact with the upper part of the holder 42 (step S104).

The technician 24 causes the imaging control device 50 to execute radiography (step S105) by operating the operation unit 16 in a case where the alignment for the subject to be examined H ends. When the radiography ends, the subject to be examined H gets off the lifting device 13 (step S106). The technician 24 confirms that the subject to be examined H has gotten off the lifting device 13, and then operates the operation unit 16 to return the lifting device 13 to the initial position (step S107). Then, the technician 24 sterilizes the portion of the holder 42 with which the chin of the subject to be examined H has come into contact (step S108). This sterilization may be performed by a device such as an ultraviolet irradiation device.

In addition, before performing the radiography, the technician 24 may adjust the irradiation range on the basis of the light irradiation field indicating the irradiation range of radiation with light, in a state in which the subject to be examined H is aligned. A light irradiation device that is used to form the light irradiation field is provided in the radiation generation device 11. The technician 24 operates the operation unit 16 to drive the collimator 32, thereby setting an appropriate irradiation range. At this time, the technician 24 can set the irradiation range while confirming the position of the irradiation range with the image P acquired by the camera 14.

Figure 11:
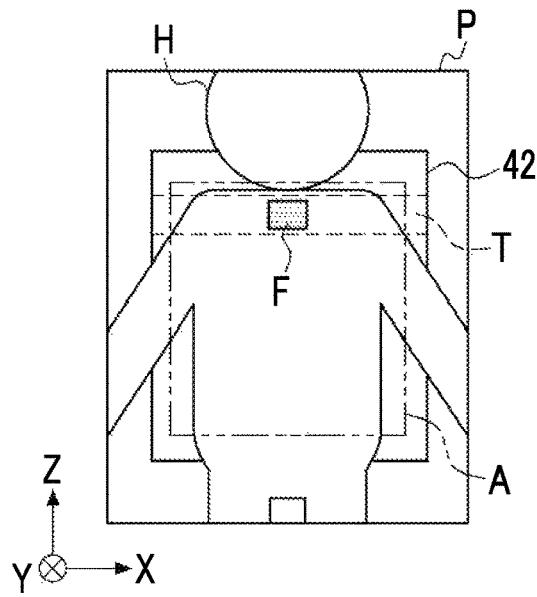
FIG. 11 is a schematic diagram showing an example of a light irradiation field appearing in an image.

FIG. 11 is an example of the light irradiation field appearing in the image P. The technician 24 can change the position or size of a light irradiation field A by operating the operation unit 16, and the collimator 32 is driven in conjunction with the change in the position or size of the light irradiation field A and the position or size of the irradiation range of radiation is changed.

A configuration may be adopted in which radiography is permitted in a case where the position and size of the light irradiation field A appearing in the image P are appropriate. Alternatively, a configuration may be adopted in which the information output unit 17 gives a warning in a case where an imaging site (for example, the chest) registered in the imaging menu does not fall within the irradiation range as a result of the adjustment of the light irradiation field A.

Third Modification Example

In a third modification example, the lifting control device 52 detects the body motion of the subject to be examined H on the basis of the lifting speed of the lifting device 13 and the change in the misalignment amount D derived by the image analysis device 51. Ideally, the change in the misalignment amount D should match the lifting speed, but the change in the misalignment amount D does not match the lifting speed due to the body motion of the subject to be examined H. The lifting control device 52 detects the difference between the lifting speed and the change in the misalignment amount D, as the body motion speed.

Since it is dangerous to lift and lower the lifting device 13 in a state in which the subject to be examined H has a large body motion, the lifting control device 52 performs lifting control of the lifting device 13 on the basis of the detected body motion speed.

Figure 12:
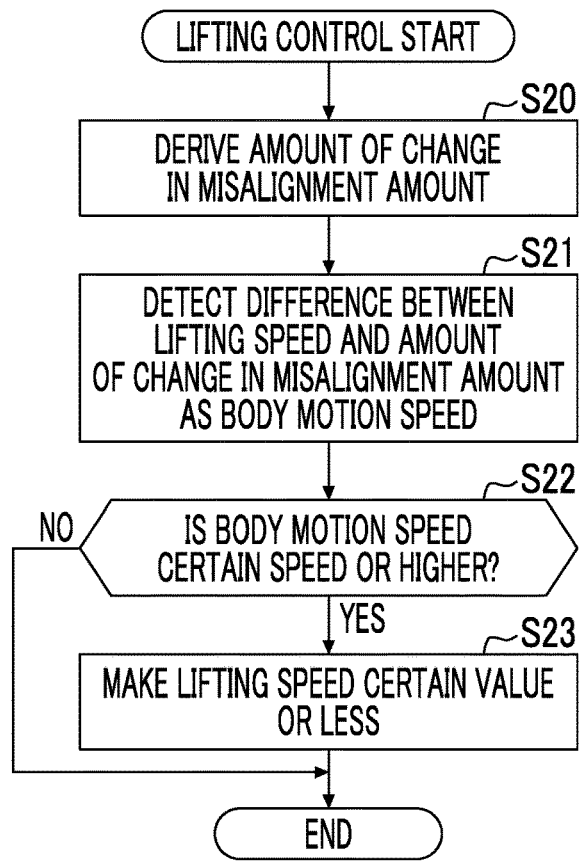
FIG. 12 is a flowchart showing lifting control according to a third modification example.

FIG. 12 shows lifting control according to the third modification example. The lifting control according to the third modification example is executed in step S15 in the flowchart shown in FIG. 7. In the present modification example, the lifting control device 52 derives an amount of change in the misalignment amount D (step S20). Next, the lifting control device 52 derives a difference between the derived misalignment amount D and the lifting speed of the lifting device 13 under control, and detects the difference as the body motion speed (step S21).

Next, the lifting control device 52 determines whether or not the detected body motion speed is a certain speed or higher (step S22). In a case where the lifting control device 52 determines that the body motion speed is a certain speed or higher (step S22: YES), the lifting control device 52 makes the lifting speed of the lifting device 13 a certain value or less (step S23). In a case where the lifting control device 52 determines that the body motion speed is not a certain speed or higher (step S23: NO), the lifting control device 52 ends the lifting control.

It should be noted that a case where the lifting speed is made a certain value or less in step S23 also includes a case where the lifting control device 52 stops lifting and lowering the lifting device 13.

As described above, according to the third modification example, the lifting speed is made a certain value or less in a case where the body motion speed is a certain speed or higher. Therefore, the lifting speed is made a certain value or less before the body motion speed is lower than a certain speed, so that the safety of the subject to be examined H when the lifting device 13 is lifted and lowered is improved.

Fourth Modification Example

In a fourth modification example, the lifting control device 52 stops lifting and lowering the lifting device 13 in a case where the subject to be examined H is predicted to collide with an object, on the basis of the image P captured by the camera 14. Here, the object is an object, such as an obstacle, except for the subject to be examined H and the holder 42. Since there is a risk that the subject to be examined H may collide with the object in a case where the object exists in the vicinity of the holder 42 in a case where the lifting device 13 is lifted and lowered in a state in which the subject to be examined H is placed thereon, the lifting control device 52 stops lifting and lowering the lifting device 13 by predicting that the subject to be examined H may collide with the object.

Figure 13:
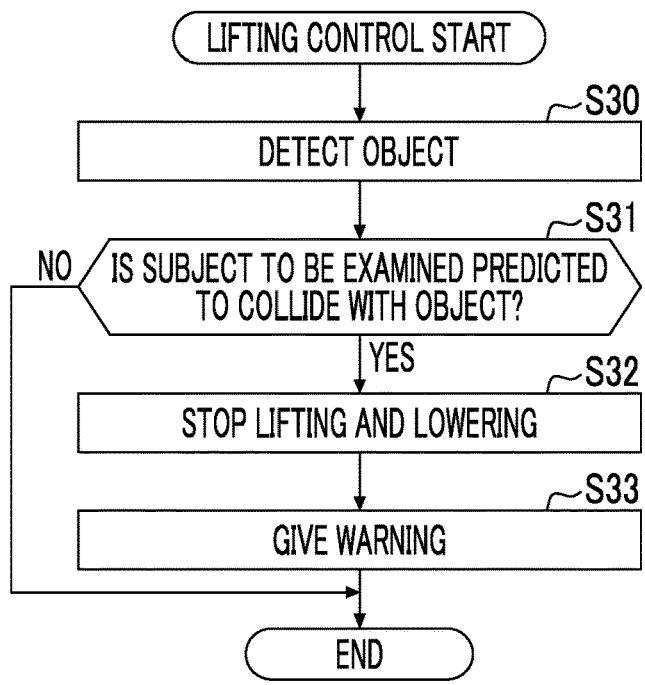
FIG. 13 is a flowchart showing lifting control according to a fourth modification example.

FIG. 13 shows lifting control according to the fourth modification example. The lifting control according to the fourth modification example is executed in step S15 in the flowchart shown in FIG. 7. In the present modification example, the image analysis device 51 detects the object, such as an obstacle, except for the subject to be examined H and the holder 42, on the basis of the image P captured by the camera 14 (step S30).

The lifting control device 52 determines whether or not the subject to be examined H is predicted to collide with the object, on the basis of the positional relationship between the object detected by the image analysis device 51 and the subject to be examined H (step S31). The lifting control device 52 stops lifting and lowering the lifting device 13 (step S32) in a case where the subject to be examined H is predicted to collide with the object (step S31: YES). Then, the lifting control device 52 gives a warning through the information output unit 17 (step S33). The warning is given through, for example, a voice output for calling attention to the technician 24. The warning may be given through a method such as the display of a message for calling attention to the technician 24.

In a case where the subject to be examined H is not predicted to collide with the object, the lifting control device 52 ends the lifting control (step S31: NO).

As described above, according to the fourth modification example, it is possible to prevent the subject to be examined H from colliding with the object because of the lifting and lowering of the lifting device 13.

Fifth Modification Example

In the above embodiment, the feature site F is set to the "vertebra prominens" and the target region T is set to the upper side of the image P, but the feature site F and the target region T are changed according to the imaging menu, in a fifth modification example.

In the fifth modification example, the feature site F and the target region T are set in advance for each imaging menu. For example, the control apparatus 15 holds a setting table 70 shown in FIG. 14 as an example. The target region T is defined by the width in the Z direction and the center coordinates.

In the fifth modification example, the image analysis device 51 selects the feature site F and the target region T for detecting the misalignment amount D, according to the imaging menu input to the imaging control device 50. Specifically, the image analysis device 51 acquires the feature site F and the target region T corresponding to the imaging menu input to the imaging control device 50 from the setting table 70, and uses the acquired feature site F and the target region T to detect the misalignment amount D.

In the above embodiments and the fifth modification example, the feature site F is set to the anatomical feature of the subject to be examined H, but a marker provided on the examination gown worn by the subject to be examined H may be set as the feature site F. The marker provided on the examination gown is, for example, a pattern image with which the image analysis device 51 can recognize the pattern.

The technique of the present disclosure can also appropriately combine the above-mentioned various embodiments and/or the above-mentioned various modification examples. In addition, it goes without saying that the technique of the present disclosure is not limited to the above embodiments and various configurations may be adopted without departing from the gist of the technique of the present disclosure.

The contents described and shown above are detailed descriptions for the parts related to the technique of the present disclosure, and are merely an example of the technique of the present disclosure. For example, the descriptions for the above configurations, functions, operations, and effects are the descriptions for an example of the configurations, functions, operations, and effects of parts related to the technique of the present disclosure. Therefore, it goes without saying that unnecessary parts may be deleted, new elements may be added, or replacements may be made with respect to the contents described and shown above, without departing from the gist of the technique of the present disclosure. In addition, in order to avoid complications and facilitate understanding of the parts related to the technique of the present disclosure, descriptions for common general knowledge and the like that do not require special descriptions for enabling the implementation of the technique of the present disclosure are omitted, in the contents described and shown above.

In the present specification, "A and/or B" has the same meaning as "at least one of A or B". That is, "A and/or B" means that only A may be used, only B may be used, or a combination of A and B may be used. In addition, in the present specification, the same concept as "A and/or B" is also applied to a case where three or more matters are expressed by "and/or".

All documents, patent applications, and technical standards described in the present specification are incorporated in the present specification by reference to the same extent as in a case where the individual documents, patent applications, and technical standards were specifically and individually stated to be incorporated by reference.

What is claimed is:

1. A radiography system comprising:
a radiation source that emits radiation;
an imaging stand having a detection panel that generates a radiation image by detecting the radiation;
a lifting device on which a subject to be examined is placed;
a misalignment amount detection device that detects a relative misalignment amount between the imaging stand and the subject to be examined; and
a lifting control device that lifts and lowers the lifting device on the basis of the misalignment amount detected by the misalignment amount detection device.

2. The radiography system according to claim 1, wherein the lifting control device controls the lifting device in a direction of lowering the lifting device from an initial position and in a direction of reducing the misalignment amount.

3. The radiography system according to claim 1, wherein the lifting control device controls a lifting speed of the lifting device according to the misalignment amount.

4. The radiography system according to claim 3, wherein the lifting control device makes the lifting speed high in a case where the misalignment amount is large, and makes the lifting speed low in a case where the misalignment amount is small.

5. The radiography system according to claim 3, wherein the lifting control device detects a body motion of the subject to be examined on the basis of the lifting speed and a change in the misalignment amount.

6. The radiography system according to claim 5, wherein the lifting control device detects a difference between the lifting speed and the change in the misalignment amount, as a body motion speed of the subject to be examined, and makes the lifting speed a certain value or less in a case where the detected body motion speed is a certain speed or higher.

7. The radiography system according to claim 1,
wherein the misalignment amount detection device includes
   a camera provided on the radiation source and imaging the subject to be examined, and
   an image analysis device that detects the misalignment amount by analyzing an image acquired by the camera.

8. The radiography system according to claim 7,
wherein the image analysis device detects a feature site of the subject to be examined from the image, and detects the misalignment amount on the basis of a difference between a position of the detected feature site and a target region on the imaging stand.

9. The radiography system according to claim 8,
wherein the feature site is an anatomical feature of the subject to be examined or a marker provided on an examination gown.

10. The radiography system according to claim 9,
wherein the feature site and the target region are set in advance for each imaging menu, and
the image analysis device selects the feature site and the target region for detecting the misalignment amount, according to the imaging menu.

11. The radiography system according to claim 7,
wherein the lifting control device stops lifting and lowering the lifting device in a case where the subject to be examined is predicted to collide with an object on the basis of the image.

12. The radiography system according to claim 7,
wherein the lifting control device gives a warning in a case where the subject to be examined is predicted to collide with an object on the basis of the image.

13. A control method of a radiography system including
a radiation source that emits radiation,
an imaging stand having a detection panel that generates a radiation image by detecting the radiation,
a lifting device on which a subject to be examined is placed, and
a misalignment amount detection device that detects a relative misalignment amount between the imaging stand and the subject to be examined,
the control method comprising:
lifting and lowering the lifting device on the basis of the misalignment amount detected by the misalignment amount detection device.

* * * * *